US011457823B2

(12) United States Patent
Chen

(10) Patent No.: US 11,457,823 B2
(45) Date of Patent: Oct. 4, 2022

(54) WEARABLE BLOOD PRESSURE DETECTING DEVICE AND DETECTING METHOD THEREOF

(71) Applicant: ASUSTEK COMPUTER INC., Taipei (TW)

(72) Inventor: Yu-Jen Chen, Taipei (TW)

(73) Assignee: ASUSTEK COMPUTER INC., Taipei (TW)

( * ) Notice: Subject to any disclaimer, the term of this patent is extended or adjusted under 35 U.S.C. 154(b) by 396 days.

(21) Appl. No.: 16/428,423

(22) Filed: May 31, 2019

(65) Prior Publication Data

US 2019/0365254 A1 Dec. 5, 2019

(30) Foreign Application Priority Data

Jun. 1, 2018 (TW) .................................. 107119001

(51) Int. Cl.
*A61B 5/021* (2006.01)
*A61B 5/00* (2006.01)
(Continued)

(52) U.S. Cl.
CPC ........ *A61B 5/02108* (2013.01); *A61B 5/0006* (2013.01); *A61B 5/02255* (2013.01);
(Continued)

(58) Field of Classification Search
CPC .... A61B 5/02108–02125; A61B 5/024; A61B 5/02416; A61B 5/02438;
(Continued)

(56) References Cited

U.S. PATENT DOCUMENTS

2007/0276632 A1* 11/2007 Banet .................. A61B 5/0004
702/187
2013/0184595 A1* 7/2013 Mukkamala ....... A61B 5/02125
600/485

(Continued)

FOREIGN PATENT DOCUMENTS

CN 103976721 A 8/2014
CN 107233087 A 10/2017
(Continued)

OTHER PUBLICATIONS

Jung et al., "Changes of Pulse Wave Velocity in Arm According to Characteristic Points of Pulse Wave," 2007 International Conference on Convergence Information Technology (ICCIT 2007), 2007, pp. 821-826, doi: 10.1109/ICCIT.2007.409. (Year: 2007).*

*Primary Examiner* — Eric F Winakur
*Assistant Examiner* — Alice Ling Zou
(74) *Attorney, Agent, or Firm* — Muncy, Geissler, Olds & Lowe, P.C.

(57) ABSTRACT

A wearable blood pressure detecting device is provided. The wearable blood pressure detecting device includes a pulse detecting module, a processing unit, a memory unit, a model selecting unit, and a blood pressure calculating unit. The pulse detecting module is configured to generate a pulse waveform. The processing unit is configured to capture the pulse waveform to generate at least one pulse characteristic value. The memory unit is configured to store at least two blood pressure models corresponding to different pulse characteristic value ranges. The model selecting unit is configured to select a corresponding blood pressure model according to the at least one pulse characteristic value. The blood pressure calculating unit is configured to calculate a blood pressure value by the selected blood pressure model.

3 Claims, 7 Drawing Sheets

(51) Int. Cl.
  *A61B 5/0225*   (2006.01)
  *A61B 5/024*   (2006.01)

(52) U.S. Cl.
  CPC .......... *A61B 5/681* (2013.01); *A61B 5/02438* (2013.01); *A61B 5/6824* (2013.01); *A61B 5/6831* (2013.01); *A61B 5/6833* (2013.01)

(58) Field of Classification Search
  CPC ....... A61B 5/0245; A61B 5/0255; A61B 5/72; A61B 5/7235; A61B 5/7275–7278; A61B 5/681; A61B 5/02007; A61B 5/02422–02433; A61B 5/02455–0255; A61B 5/0285; A61B 5/02–02007; A61B 5/021–02125; A61B 5/2416; A61B 5/02427; A61B 5/02444–0245; A61B 5/7239; A61B 5/7264–7267; A61B 5/7278; A61B 5/02035
  See application file for complete search history.

(56) References Cited

U.S. PATENT DOCUMENTS

| | | | |
|---|---|---|---|
| 2013/0324866 A1* | 12/2013 | Gladshtein | A61B 5/0285 600/507 |
| 2017/0109495 A1* | 4/2017 | Xin | A61B 5/7264 |
| 2017/0340219 A1* | 11/2017 | Sullivan | A61B 5/681 |
| 2018/0192900 A1 | 7/2018 | Wei | |
| 2018/0303354 A1* | 10/2018 | Li | A61B 5/7278 |
| 2019/0175042 A1* | 6/2019 | Wang | A61B 5/6801 |

FOREIGN PATENT DOCUMENTS

| | | | | |
|---|---|---|---|---|
| CN | 107847153 A | 3/2018 | | |
| WO | WO-2008154647 A1 * | 12/2008 | ......... | A61B 5/02007 |
| WO | WO-2017171632 A1 * | 10/2017 | ......... | A61B 5/02108 |
| WO | WO-2018102486 A1 * | 6/2018 | ............ | A61B 5/021 |

* cited by examiner

WEARABLE BLOOD PRESSURE DETECTING DEVICE AND DETECTING METHOD THEREOF

CROSS-REFERENCE TO RELATED APPLICATION

This application claims the priority benefit of Taiwan Application Serial No. 107119001, filed on Jun. 1, 2018. The entirety of the above-mentioned patent application is hereby incorporated by reference herein and made a part of specification.

BACKGROUND OF THE INVENTION

Field of the Invention

The disclosure relates to a blood pressure detecting device and a detecting method thereof, and more particularly, to a wearable blood pressure detecting device and a detecting method thereof.

Description of the Related Art

A traditional wearable blood pressure detecting device detects a pulse wave velocity (PWV), and then acquires measured blood pressure values according to the same group of blood pressure calculating models built based on a relation between the pulse wave velocity and blood pressure. However, different subjects are usually found in practice that, although the same pulse wave velocity is detected, due to differences of blood flow characteristics (such as, blood vessel size, elasticity and blood concentration), different blood pressure values exist. Under this circumstance, when a traditional wearable blood pressure detecting device is used, differences between the subjects are not effectively distinguished, and errors are generated easily, which affects accuracy of blood pressure detecting.

BRIEF SUMMARY OF THE INVENTION

The disclosure provides a wearable blood pressure detecting device. The wearable blood pressure detecting device includes a pulse detecting module, a processing unit, a memory unit, a model selecting unit, and a blood pressure calculating unit. The pulse detecting module is configured to generate a pulse waveform. The processing unit is configured to capture the pulse waveform to generate at least one pulse characteristic value. The memory unit is configured to store at least two blood pressure models corresponding to different pulse characteristic value ranges. The model selecting unit is configured to select the corresponding blood pressure model according to the at least one pulse characteristic value. The blood pressure calculating unit is configured to calculate a blood pressure value by the selected blood pressure model.

The disclosure provides a blood pressure detecting method. The blood pressure detecting method includes the following steps: providing a pulse waveform; generating at least one pulse characteristic value based on the pulse waveform; providing at least two blood pressure models corresponding to different pulse characteristic value ranges; selecting the corresponding blood pressure model based on the at least one pulse characteristic value; and calculating a blood pressure value by using the selected blood pressure model.

A traditional wearable blood pressure detecting device estimates the blood pressure value just based on a singular condition of a pulse wave velocity, blood flow characteristics of various to-be-tested persons are not effectively distinguished, and errors are easily generated, which affects accuracy of blood pressure detecting. In comparison, the wearable blood pressure detecting device and the detecting method thereof provided by the disclosure distinguish the blood flow characteristics of the different to-be-tested persons based on the pulse characteristic value, a proper blood pressure model is fast screened out, and the accuracy of blood pressure detecting is improved easily.

Specific embodiments of the disclosure will be further described by using the following examples and drawings.

DETAILED DESCRIPTION OF THE EMBODIMENTS

Specific embodiments of the disclosure will be described in further detail below with reference to schematic drawings. The advantages and features of the disclosure will become more apparent from the following description and claims. It should be noted that the drawings are all in a very simplified form and are not drawn to accurate scale, but are merely used for convenience and clarity of description of the embodiments of the disclosure.

Figure 1:
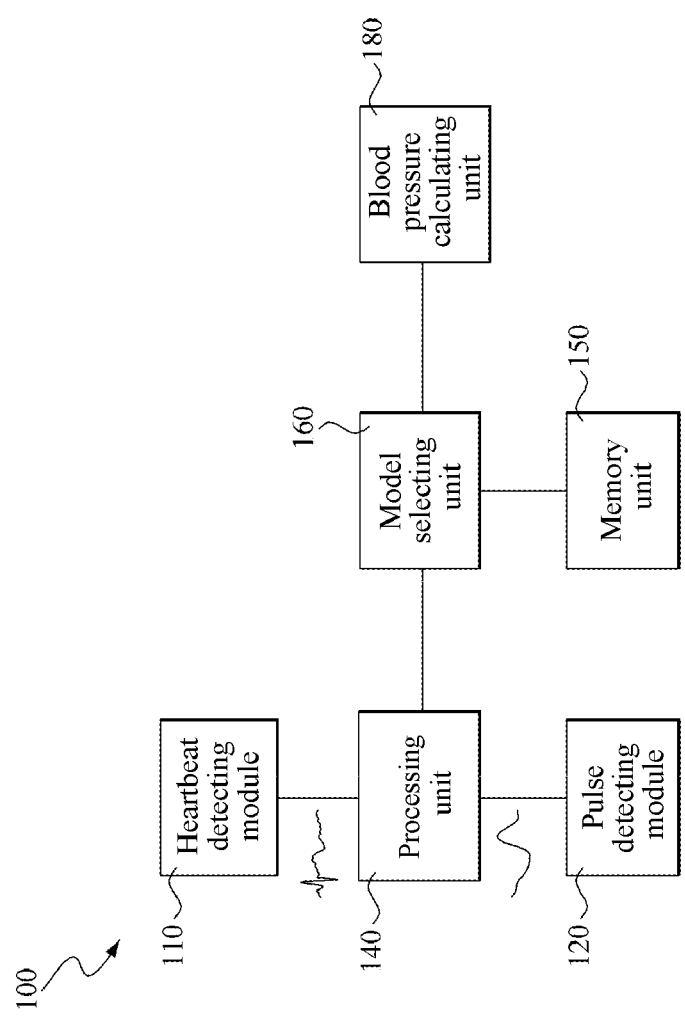
FIG. 1 is a block schematic view of an embodiment of a wearable blood pressure detecting device according to the disclosure.

FIG. 1 is a block schematic view of an embodiment of a wearable blood pressure detecting device according to the disclosure. The wearable blood pressure detecting device 100 is an electronic watch, an electronic bracelet, a skin patch or other electronic devices being wearable or making contact with a human body to detect a pulse.

As shown in the figure, the wearable blood pressure detecting device 100 includes a heartbeat detecting module 110, a pulse detecting module 120, a processing unit 140, a memory unit 150, a model selecting unit 160 and a blood pressure calculating unit 180.

The heartbeat detecting module 110 is configured to generate a heartbeat waveform, such as an electrocardiography (ECG) waveform. The pulse detecting module 120 is configured to generate a pulse waveform, such as a photoplethymography (PPG) waveform. A technology for detecting heartbeat and pulse to generate a heartbeat waveform and a pulse waveform is commonly known in the technical field, and is not repeated herein. By comparing the heartbeat waveform and the pulse waveform, a pulse transit time (PTT) of a to-be-tested person is estimated, and then a pulse wave velocity (PWV) is calculated.

The processing unit 140 is configured to capture the pulse waveform to generate at least one pulse characteristic value corresponding to the captured pulse waveform. More detailed illustration is provided for a relation between the pulse waveform and the pulse characteristic value in a subsequent section corresponding to FIG. 3.

The memory unit 150 stores at least two groups of blood pressure models for selection. The blood pressure model is used for displaying a corresponding relation of the pulse wave velocity and a blood pressure value, and the blood pressure models correspond to different pulse characteristic value ranges. Due to assistance of the blood pressure model, the wearable blood pressure detecting device 100 calculates a corresponding blood pressure value based on the detected pulse wave velocity immediately. More detailed illustration is provided for building of the blood pressure model in a subsequent section corresponding to FIG. 4.

The model selecting unit 160 selects the corresponding blood pressure model according to the at least one pulse characteristic value estimated by the processing unit 140. Specifically speaking, the model selecting unit 160 compares the pulse characteristic value of the to-be-tested person and the pulse characteristic value ranges corresponding to the various blood pressure models, and the blood pressure model corresponding to the range is selected and used on calculation of the blood pressure value. Basically, the blood pressure model selected by the model selecting unit 160 is the blood pressure model built by a detecting sample belonging to a same group with the pulse characteristic value of the to-be-tested person.

The blood pressure calculating unit 180 calculates a blood pressure value of the to-be-tested person based on the pulse wave velocity of the to-be-tested person by using the blood pressure model selected by the model selecting unit 160.

Figure 2:
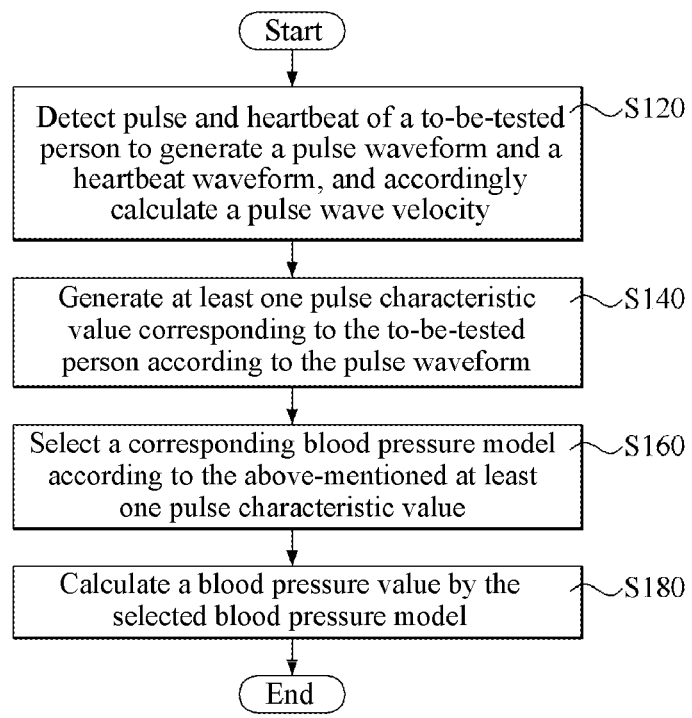
FIG. 2 is a flow chart of an embodiment of a blood pressure detecting method according to the disclosure.

FIG. 2 is a flow chart of an embodiment of a blood pressure detecting method according to the disclosure. The flow chart displays a procedure when the wearable blood pressure detecting device 100 of FIG. 1 is utilized for detecting a blood pressure. The blood pressure detecting method includes the following steps.

Firstly, in step S120, the pulse detecting module 120 is configured to detect the pulse of the to-be-tested person to generate a pulse waveform, and the heartbeat detecting module 100 is configured to detect the heartbeat of the to-be-tested person to generate a heartbeat waveform. Meanwhile, by comparing the heartbeat waveform and the pulse waveform, a pulse transit time (PTT) is estimated, and then a pulse wave velocity (PWV) is calculated.

Next, in step S140, the processing unit 140 is configured to generate at least one corresponding pulse characteristic value based on the pulse waveform of the to-be-tested person. More detailed illustration is provided for a relation of the pulse waveform and the pulse characteristic value in a subsequent section corresponding to FIG. 3.

Then, in step S160, the model selecting unit 160 is configured to select a corresponding blood pressure model from a plurality of groups of preset blood pressure models according to the at least one obtained pulse characteristic value. The blood pressure models are pre-stored in the memory unit 150 of the wearable blood pressure detecting device 100. In an embodiment, the blood pressure model is configured to display a corresponding relation of the pulse wave velocity and the blood pressure value, and the blood pressure models correspond to a specific pulse characteristic value range.

Finally, in step S180, the blood pressure calculating unit 180 is configured to calculate a blood pressure value of the to-be-tested person based on the calculated pulse wave velocity by the blood pressure model selected in step S160.

The pulse wave velocity is first calculated in the above-mentioned embodiment, and after the blood pressure model is selected, the calculated pulse wave velocity is utilized for calculating the blood pressure value. In another embodiment, a corresponding pulse characteristic value is generated based on the heartbeat waveform and the pulse waveform, and then after the blood pressure model is selected, the pulse characteristic value is directly utilized for calculating the blood pressure value.

Figure 3:
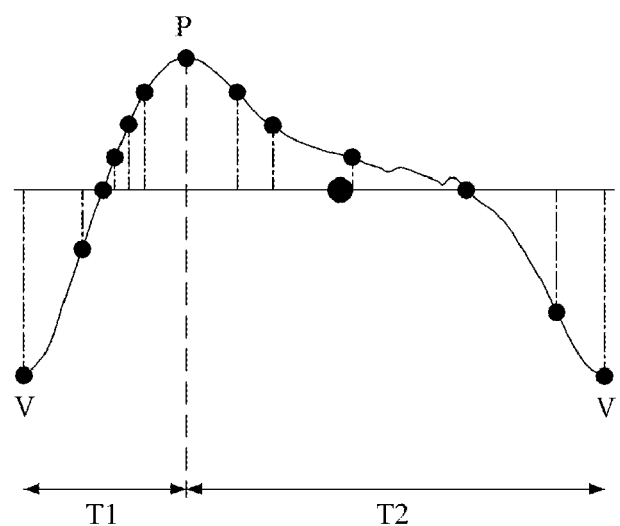
FIG. 3 is a schematic view of a first embodiment of a pulse waveform and a pulse characteristic value captured based on the pulse waveform of the disclosure.

FIG. 3 is a schematic view of a pulse waveform and a pulse characteristic value generated based on the pulse waveform in a first embodiment of the disclosure.

As shown in FIG. 3, with a wave peak P of the pulse waveform as a criterion, a wave peak P front width T1 and a wave peak rear width T2 are captured in the embodiment, and a square of a ratio of the wave peak front width T1 to the wave peak rear width T2 of the pulse waveform is used as the pulse characteristic value. The wave peak front width T1 of the embodiment is defined as a distance from the wave peak P to the front adjacent wave trough V of the wave peak P, and the wave peak rear width T2 is defined as a distance from the wave peak P to the rear adjacent wave trough V of the wave peak P. A calculating manner of positions of the wave peak P and the wave trough V is commonly known in the technical field, and is not repeated herein.

Secondly, according to an actual data distribution state (which is affected by factors such as the race and the gender of the to-be-tested person), the disclosure also utilizes the wave peak front width T1 of the pulse waveform, the wave peak rear width T2 of the pulse waveform, or the ratio of the wave peak front width T1 of the pulse waveform to the wave peak rear width T2 of the pulse waveform as the pulse characteristic value, and also uses a plurality of pulse characteristic values simultaneously, and in an embodiment, the wave peak front width T1 and the wave peak rear width T2 of the pulse waveform are used at the same time to serve as pulse characteristic values.

As shown in FIG. 1 and FIG. 2, the model selecting unit 160 selects the corresponding blood pressure model in a plurality of groups of preset blood pressure models according to the obtained at least one pulse characteristic value. A method for generating the blood pressure model is illustrated below.

Figure 4:
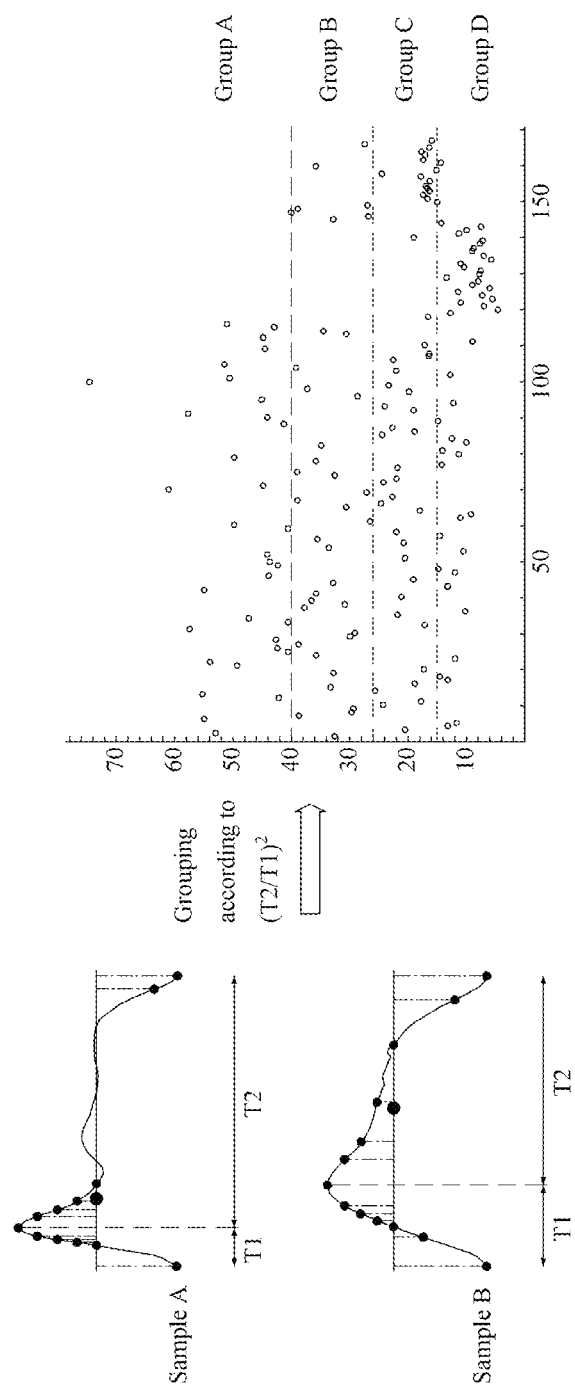
FIG. 4 is a schematic view of an embodiment building a plurality of groups of blood pressure models based on the pulse characteristic value of FIG. 3 according to the disclosure.

FIG. 4 displays a plurality of groups of blood pressure models built based on the pulse characteristic value of FIG. 3. As shown in FIG. 4, generally speaking, due to an individual difference, pulse characteristic values detected according to the pulse waveform obvious differ from each other. The square of the ratio of the wave peak rear width T2 to the wave peak front width T1 of the pulse waveform is used as the pulse characteristic value, a sample A and a sample B shown in the figure are drawn, and it is seen that a pulse characteristic value of the sample A is obviously larger than a pulse characteristic value of the sample B. The embodiment is set to distinguish detecting samples into four groups according to a value range of the pulse characteristic value (namely, the square of the ratio of the wave peak rear width T2 to the wave peak front width T1 of the pulse waveform), so as to build four different blood pressure models: a group A, a group B, a group C and a group D.

In an embodiment, when the blood pressure model is built, it is needed to build a blood pressure model corresponding to the group in manners of regression analysis, or machine learning or the like for detecting sample data, such as the pulse characteristic value, the pulse wave velocity and an actual detected blood pressure value, of the same group. In an embodiment, the blood pressure model is an equation including a pulse characteristic value variable. When a blood pressure is calculated, by inputting the pulse characteristic value of the to-be-tested person, a corresponding blood pressure value is estimated. Besides the pulse characteristic value provided by the first embodiment, according to characteristics of the pulse waveform, in other embodiments, other pulse characteristic values are also selected to build the blood pressure model, so as to facilitate detection of the blood pressure.

Figure 5A:
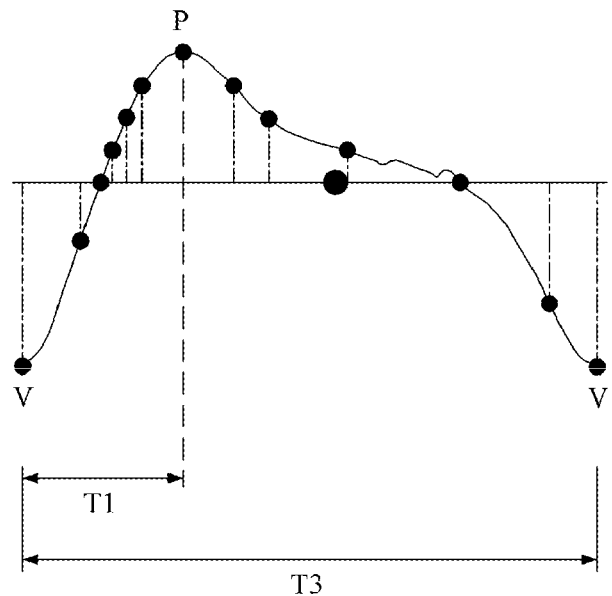
FIG. 5A is a schematic view of a second embodiment of the pulse characteristic value captured based on the pulse waveform according to the disclosure.

FIG. 5A is a schematic view of a second embodiment of the disclosure. As shown in the figure, different from the first embodiment, a wavelength T3 of the pulse waveform and the wave peak front width T1 are captured in the embodiment, and a ratio of the wave peak front width T1 to the wavelength T3 is used as the pulse characteristic value.

Figure 5B:
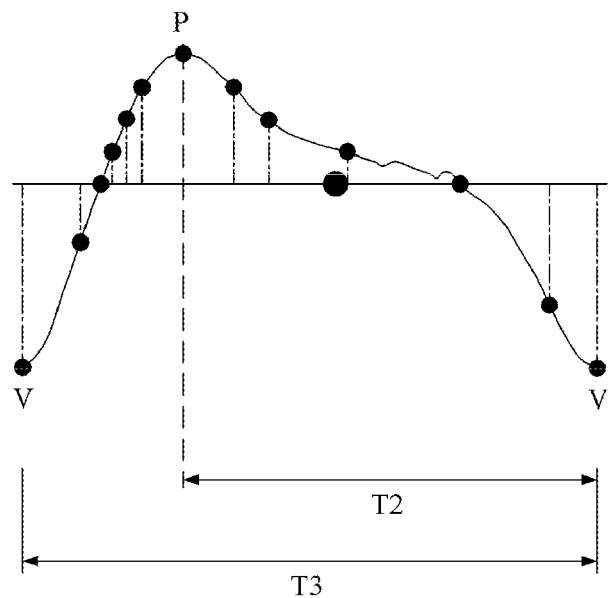
FIG. 5B is a schematic view of a third embodiment of the pulse characteristic value captured based on the pulse waveform according to the disclosure.

FIG. 5B is a schematic view of a third embodiment of the disclosure. Different from the first embodiment, a wavelength T3 of the pulse waveform and the wave peak rear width T2 are captured in the embodiment, and a ratio of the wave peak rear width T2 to the wavelength T3 is used as the pulse characteristic value.

Figure 5C:
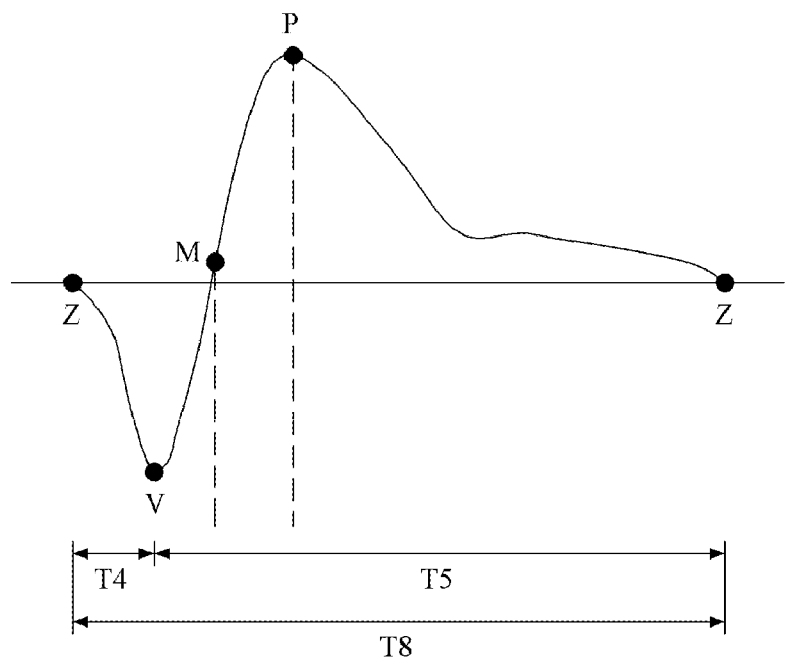
FIG. 5C is a schematic view of a fourth embodiment of the pulse characteristic value captured based on the pulse waveform according to the disclosure.

FIG. 5C is a schematic view of a fourth embodiment of the disclosure. Different from the first embodiment, a wave trough front width T4 of the pulse waveform and a wave trough rear width T5 of the pulse waveform are captured in the embodiment as the pulse characteristic values. In addition, different from the first embodiment in which a wave trough V is used as a dividing point of a complete waveform, the embodiment uses a zero-crossing point Z as a dividing point to define a wavelength T8. Basically, a length of the wavelength T8 should be equal to a length of the wavelength T3.

In the embodiment, the wave trough front width T4 is defined as a distance from the wave trough V to the front zero-crossing point Z of the wave trough V, and the wave trough rear width T5 is defined as a distance from the wave trough V to the rear zero-crossing point Z of the wave trough V. In an embodiment, according to the actual data distribution state, the wave peak is also selected as the dividing point of the complete waveform, the wave trough front width is defined as a distance from the wave trough to the front adjacent wave peak of the wave trough, and the wave trough rear width is defined as a distance from the wave trough to the rear adjacent wave peak of the wave trough. A calculating manner of a position of the zero-crossing point Z is commonly known in the technical field, and is not repeated herein.

In addition, similar with the above-mentioned second and third embodiments, in other embodiments of the disclosure, a ratio of the wave trough front width T4 to the wavelength T8 or a ratio of the wave trough rear width T5 to the wavelength T8 is also utilized as the pulse characteristic value.

Figure 5D:
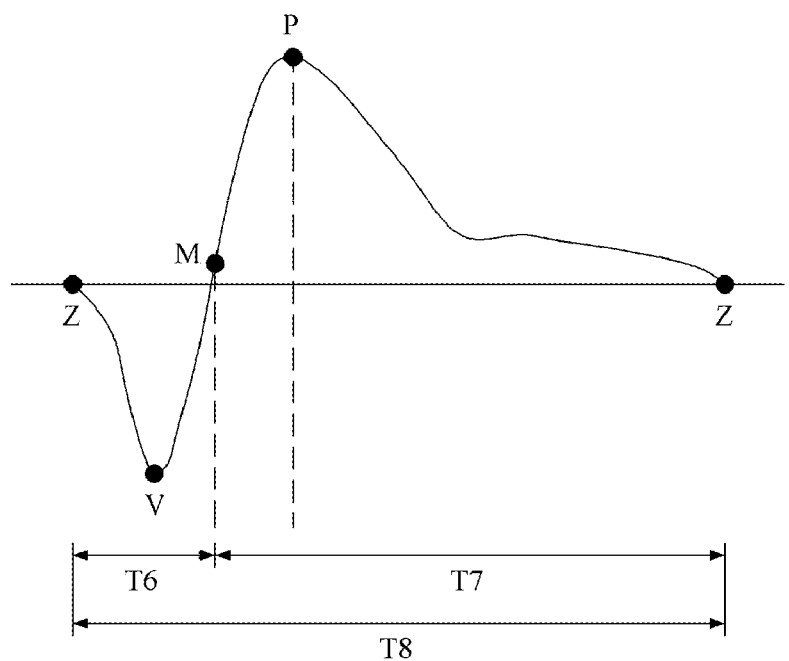
FIG. 5D is a schematic view of a fifth embodiment of the pulse characteristic value captured based on the pulse waveform according to the disclosure.

FIG. 5D is a schematic view of a fifth embodiment of the disclosure. Different from the fourth embodiment in which the wave trough front width T4 of the pulse waveform and the wave trough rear width T5 of the pulse waveform are captured to calculate the pulse characteristic value, a front width T6 of a maximum slope point M of the pulse waveform and a rear width T7 of the maximum slope point M are captured in the embodiment to serve as the pulse characteristic values. The front width T6 of the maximum slope point M of the embodiment is defined as a distance from the maximum slope point M to the front zero-crossing point Z of the maximum slope point M, and the rear width T7 of the maximum slope point M is defined as a distance from the maximum slope point M to the rear zero-crossing point Z of the maximum slope point M. A calculating manner of the maximum slope point M is commonly known in the technical field, and is not repeated herein.

Similar with the above-mentioned second and third embodiments, in other embodiments of the disclosure, a ratio of the front width T6 of the maximum slope point M to the wavelength T8 or a ratio of the rear width T7 of the maximum slope point M to the wavelength T8 is also utilized as the pulse characteristic value.

Figure 6:
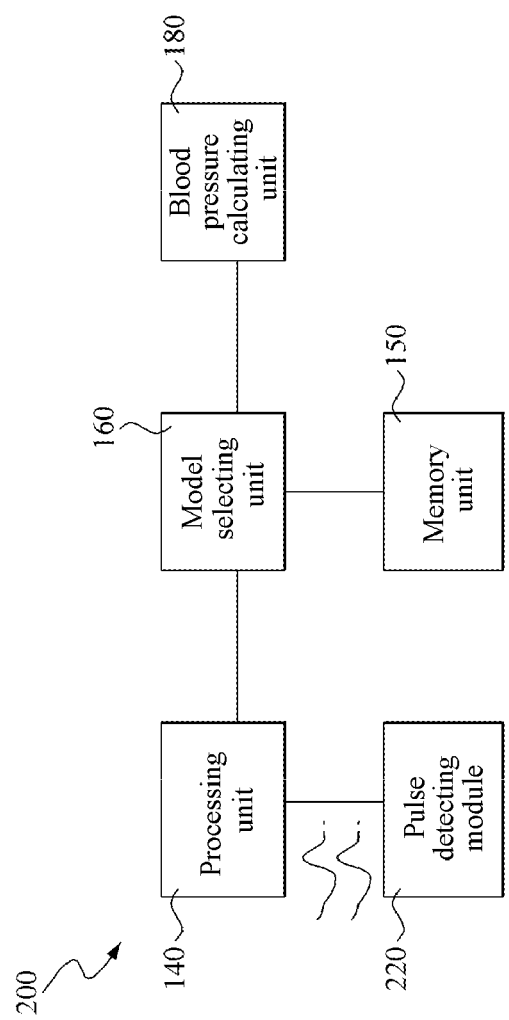
FIG. 6 is a block schematic view of another embodiment of the wearable blood pressure detecting device according to the disclosure.

FIG. 6 is a block schematic view of another embodiment of the wearable blood pressure detecting device of the disclosure. A main difference of the wearable blood pressure detecting device 200 and the blood pressure detecting device 100 of FIG. 1 lies in that the blood pressure detecting device 200 of the embodiment omits a heartbeat detecting module, and data detected by a pulse detecting module 220 is directly used for estimating a pulse wave velocity and a pulse characteristic value. Specifically speaking, the pulse detecting module 220 of the embodiment includes two detectors so as to estimate the pulse wave velocity of the to-be-tested person. In the case of an embodiment, the pulse waveform is a photoplethymography waveform. According to a spacing distance of the two pulse waveforms and the two detectors, the pulse wave velocity of the to-be-tested person is estimated.

A traditional wearable blood pressure detecting device estimates the blood pressure value just based on the pulse wave velocity, blood flow characteristics of various to-be-tested persons are not effectively distinguished according to values, and errors are easily generated, which affects accuracy of blood pressure detecting. In comparison, the wearable blood pressure detecting device and the detecting method thereof provided by the disclosure distinguish the blood flow characteristics of the different to-be-tested persons based on the pulse characteristic value, an accurate blood pressure value is calculated fast according to the corresponding blood pressure model, and the accuracy of blood pressure detecting is improved easily.

The foregoing descriptions are merely preferred embodiments of the disclosure and are not intended to limit the disclosure in any way. Any person skilled in the art can make any form of equivalent replacement or modification to the technical means and technical contents disclosed by the disclosure without departing from the scope of the technical means of the disclosure, and such equivalent replacement or modification does not depart from the contents of the technical means of the present disclosure and still falls within the protection scope of the disclosure.

What is claimed is:

1. A blood pressure detecting method, comprising:
providing a pulse waveform;
generating at least one pulse characteristic value based on the pulse waveform;

providing at least two blood pressure models, wherein the blood pressure models correspond to different pulse characteristic value ranges;

selecting the corresponding blood pressure model based on the at least one pulse characteristic value; and calculating a blood pressure value by using the selected blood pressure model;

wherein the blood pressure models are configured to relate pulse wave velocity to a corresponding blood pressure value;

wherein the pulse characteristic value comprises a front width of a maximum slope point of the pulse waveform and a rear width of the maximum slope point.

2. The blood pressure detecting method according to claim 1, wherein the blood pressure models are built through regression analysis or machine learning.

3. The blood pressure detecting method according to claim 1, further comprising:

providing a heartbeat waveform;

wherein the at least one pulse characteristic value is generated based on the pulse waveform and the heartbeat waveform.

\* \* \* \* \*